US008173966B2

(12) United States Patent
Caruba

(10) Patent No.: US 8,173,966 B2
(45) Date of Patent: May 8, 2012

(54) COLLIMATOR STORAGE APPARATUS INTEGRATED WITH PATIENT SUPPORT

(75) Inventor: James Frank Caruba, Bartlett, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1609 days.

(21) Appl. No.: 11/165,964

(22) Filed: Jun. 24, 2005

(65) Prior Publication Data

US 2006/0020201 A1 Jan. 26, 2006

(51) Int. Cl.
*A47B 23/00* (2006.01)
(52) U.S. Cl. .................. 250/363.05; 5/601; 250/363.1
(58) Field of Classification Search ............ 250/363.05, 250/363.1; 5/600, 601
See application file for complete search history.

(56) References Cited

U.S. PATENT DOCUMENTS

| 3,652,852 | A | * | 3/1972 | Miyazawa et al. ............ 378/63 |
| 4,865,284 | A | | 9/1989 | Gosis et al. |
| 5,013,018 | A | * | 5/1991 | Sicek et al. ................. 5/601 |
| 5,083,331 | A | * | 1/1992 | Schnelle et al. .............. 5/600 |
| 5,519,223 | A | * | 5/1996 | Hug et al. ................ 250/363.1 |
| 6,094,760 | A | * | 8/2000 | Nonaka et al. ................ 5/601 |
| 6,398,409 | B1 | * | 6/2002 | Brooks ...................... 378/209 |
| 6,590,214 | B1 | * | 7/2003 | Karmalawy ............. 250/363.1 |
| 6,906,328 | B2 | * | 6/2005 | Garrard et al. ........... 250/363.1 |
| 7,120,223 | B2 | * | 10/2006 | Nafstadius ................... 378/20 |
| 2004/0102690 | A1 | * | 5/2004 | Bartels et al. ............... 600/407 |
| 2005/0080331 | A1 | * | 4/2005 | Burckhardt et al. ......... 600/411 |
| 2005/0152503 | A1 | * | 7/2005 | Rauh ......................... 378/209 |
| 2005/0276383 | A1 | * | 12/2005 | Bertram et al. ............. 378/181 |
| 2007/0013273 | A1 | * | 1/2007 | Albert et al. ................ 312/209 |

* cited by examiner

*Primary Examiner* — David Porta
*Assistant Examiner* — Yara Green
(74) *Attorney, Agent, or Firm* — Peter Kendall

(57) ABSTRACT

According to some embodiments, a patient support system for a nuclear medical imaging system is provided that includes: a patient support; a collimator storage unit located under the patient support; a first support means for supporting substantially all of the weight of the collimator storage unit; and a second support means for supporting the patient support at least at a position distal from a gantry of the nuclear medical imaging system. In some embodiments, the first support means includes means for supporting the patient support at a position proximate a gantry of the nuclear medical imaging system and the second support means includes two vertical support structures. In addition, the system preferably includes at least one laterally extendable frame member mounted between the two vertical support structures.

31 Claims, 10 Drawing Sheets

COLLIMATOR STORAGE APPARATUS INTEGRATED WITH PATIENT SUPPORT

BACKGROUND

1. Field of the Invention

The present invention relates to, inter alia, medical imaging systems, and, in particular, to the handling of, e.g., collimators for gamma cameras of nuclear medicine imaging systems and/or the like. More particularly, some preferred embodiments of the invention relate to methods and apparatuses for the transfer, removal, mounting and/or storage of collimators in nuclear medicine imaging systems.

2. Background Discussion

Nuclear medicine imaging typically involves the assessment of a radionuclide distribution within a patient after the in vivo administration of radiopharmaceuticals. Imaging systems that assess radionuclide distribution include radiation detectors and acquisition electronics. Typically, the imaging systems detect x-ray or gamma ray photons derived from the administered radionuclides. Single photon emission imaging and coincidence imaging are two forms of nuclear medicine imaging that are currently in common use. In single photon emission imaging, the radionuclide itself directly emits the radiation to be assessed. For example, in Single Photon Emission Computed Tomography (SPECT), γ-emitting radionuclides such as $^{99m}$Tc, $^{123}$I, $^{67}$Ga and $^{111}$In may be part of the administered radiopharmaceutical.

Detectors used in such single photon emission imaging often use collimators placed between the patient and the gamma ray camera of the detector. In general, the collimators help to eliminate substantially all photons but those photons traveling in a desired direction. For example, a parallel hole collimator helps to eliminate photons traveling in all directions except those almost perpendicular to the surface of the detector. The energy of emitted photons as well as their location of origin may then be accumulated until a satisfactory image is obtained.

Coincidence imaging helps to eliminate the need for such a collimator by relying on the detection of two photons at different detectors at nearly the same time. An example of coincidence imaging in current clinical use is Positron Emission Tomography (PET).

Typically, radiation detectors used in nuclear medicine imaging need to absorb x- or gamma-ray photons in an energy range typically between 1 keV and several MeV. These imaging photons are the photons either directly emitted or resulting from radionuclides within a patient. In order to stop imaging photons of these energies with a collimator in SPECT imaging, a material with a high density and a high atomic number (Z) is necessary. Lead is the most common material used for collimators, but other materials such as tungsten may also be used.

Radiation detectors for SPECT imaging systems often have the ability to use collimators which may be mounted or removed from the system detectors. These "mountable" detectors are useful because a collimator with a different geometry may yield higher quality images in different situations. Being able to "swap in" a collimator with a specific geometry is, thus, highly advantageous.

As mentioned above, collimators typically need to be made of a material with a high density and a high atomic number in order to effectively stop imaging photons. These materials, such as lead, are very heavy. For example, a typical lead collimator may weigh on the order of several hundred kilograms. This high weight creates many problems for the effective and efficient imaging of patients when collimators which are mountable are in use. One problem is the risk of damage to either the gamma camera system within the detector, or even damage the collimator itself, when physically removing or mounting the collimator into the detector. Another problem is the risk of problems for the medical technician performing the mounting and/or removal of the collimator. Another problem is the time required to remove an old collimator and mount a new one in a detector. The time requirements of these procedures increases the set up time for a patient scan and reduces the throughput of patients of an imaging system, a determining factor in the profitability of an imaging system. In addition, transferring a collimator from a storage location to the imaging system may also increase the set up time for a patient scan. Another problem is that bulky and heavy collimators often require additional floor space for storage. Additionally, removing and mounting collimators often requires that components of an imaging system, such as a patient handling system, be moved from their standard operating position. This can also increase the time required for patient setup.

Various attempts have been made to address the above problems. However, none of the currently available solutions adequately address the problems of using mountable collimators. There remains a need in the nuclear medicine imaging art for systems and methods of reducing the danger, time, space, and expense of using modular collimators. There also remains a need in the art for improved methods that integrate improved systems with existing systems without substantial increases in weight and/or cost.

SUMMARY OF THE PREFERRED EMBODIMENTS

The preferred embodiments of the present invention can significantly improve upon existing methods and/or apparatuses.

According to some embodiments of the invention, a modular patient support system for nuclear medical imaging applications is provided that includes: a patient support; a plurality of support structures for supporting the patient support; wherein at least one of the support structures is modularly removable or connectable to the modular patient support system to accommodate an option change of the nuclear medical imaging system. Preferably, the support structures include vertical drives. In addition, preferably, the option change is the addition or removal of a collimator server.

According to other embodiments of the invention, an assembly of modular components for nuclear imaging applications is provided that includes: a patient support; at least one vertical support structure supporting the patient support in a first use condition of a nuclear medical imaging system; at least one modular vertical support structure connectable to support the patient support along with the at least one vertical motion support structure in a second use condition of a nuclear medical imaging system. In some embodiments, the first use condition is a condition without an automated collimator changer and the second use condition is a condition with an automated collimator changer. Preferably, the at least one modular vertical support structure includes a drive motor and the at least one vertical support structure includes a pulley driven by the drive motor. In some preferred embodiments, the at least one vertical support structure includes a plurality of vertical support structures that are connected together via at least one lateral frame member that adjusts in length to accommodate different vertical support structure use positions. In some examples, each the at least one lateral frame member telescopes to adjust in length.

According to some other embodiments, a patient support system for a nuclear medical imaging system is provided that includes: a patient support; an integrated automated collimator changer storage unit located under the patient support and supported substantially by a first vertical motion support structure; and at least one other vertical motion support structure supporting an end of the patient support distal from the nuclear medical imaging system. In some embodiments, the integrated automated collimator changer storage unit includes a support for the patient support. Preferably, the at least one other vertical motion support structure includes two vertical motion support structures, one driven via a first motor and one driven via a pulley, and wherein the first vertical motion support structure is driven via a second motor.

According to yet some other embodiments, a method of modifying a patient support system without an integrated collimator server to create a patient support system with an integrated collimator server is provided that includes:

a. providing a patient support for an imaging system and at least one vertical motion support structure supporting the patient support in a first use condition without an integrated collimator server;

b. modifying the patient support system to include an integrated collimator server underneath the patient support by adding at least one additional vertical motion support structure underneath the patient support that supports a substantially portion of the weight of a collimator server located underneath the patient support and that helps support a portion of the patient support proximate a gantry. In some embodiments, the step of modifying includes upgrading an existing patient support system after purchase and receipt by a consumer. In other embodiments, the step of modifying includes adapting a patient support system before purchase by a consumer.

In some embodiments, the step of modifying further includes laterally moving at least one of the at least one vertical motion support structure supporting the patient support from the first use condition without an integrated collimator server to a second use condition with an integrated collimator server. Preferably, the at least one vertical motion support structure supporting the patient support includes plural vertical motion support structures, including a first driven via a motor and a second driven via a pulley. In preferred embodiments, the patient support is a patient bed and wherein the integrated collimator server includes an upper pallet support for supporting a gantry side of the bed during imaging.

According to yet some other embodiments, a method of integrating an automated collimator change storage device with a patient support system is provided that includes: a) providing a patient support; b) providing a plurality of vertical support structures underneath the patient support with: i) a first of the plurality of vertical support structures supporting a substantial portion of the weight of an automated collimator change storage device underneath the patient support at a location proximate to a gantry of a nuclear medical imaging system; and ii) a second of the plurality of vertical support structures supporting at least a portion of the patient support at a location distal from a gantry of a nuclear medical imaging system. Preferably, the first and second of the plurality of vertical support structures include separate drives. In some preferred embodiments, the separate drives include separate drive motors that rotate respective vertical screw shafts. In some embodiments, a control system is provided that is configured to operate the drive motors in tandem, and, in some embodiments, a control system is provided that is configured to operate the drive motors in tandem and independently, such that the automated collimator change storage device moves either in tandem with or independently from the patient support. In some examples, the control system can be configured to move support members of the vertical support structures such that positions of the support members can be coordinated using at least one of a) a lookup table, b) an encoder, c) a pressure or strain gauge and d) a position detector.

According to yet some other embodiments, a nuclear medicine imaging system is provided that includes: a gantry; a detector attached to the gantry, having a gamma camera and at least one collimator location; a patient handling system having a patient support; a collimator server integrated into the patient handling system and storing a number of collimators beneath the patient support, the collimator server including an independent support that supports substantially all of the weight of the collimator server; the collimator server being adapted to enable i) loading of collimators into the collimator location, ii) removing collimators from the collimator location, and iii) storing collimators beneath the patient support. Preferably, the collimator server further includes means for supporting the patient support at a position proximate to the gantry.

In some embodiments, the independent support includes a vertical support structure having an independent vertical drive mechanism from a vertical drive mechanism of a vertical support structure that supports the patient support at a position distal from the gantry. Preferably, the independent support for the collimator server supports a substantial portion of the weight of all collimators stored thereon as well as a portion of the patient support so as to limit deflection of the patient support.

According to yet some other embodiments, a patient support system for a nuclear medical imaging system is provided that includes: a patient support; a collimator storage unit located under the patient support; a first support means for supporting substantially all of the weight of the collimator storage unit; and a second support means for supporting the patient support at least at a position distal from a gantry of the nuclear medical imaging system. Preferably, the first support means includes means for supporting the patient support at a position proximate a gantry of the nuclear medical imaging system. In some embodiments, the second support means includes two vertical support structures. In some embodiments, the system further includes at least one laterally extendable frame member mounted between the two vertical support structures.

The above and/or other embodiments, aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention, as well as further objects, features and advantages of the preferred embodiments will be more fully understood with reference to the following detailed description of the preferred embodiments, when taken in conjunction with the accompanying drawings, wherein.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Figure 1:
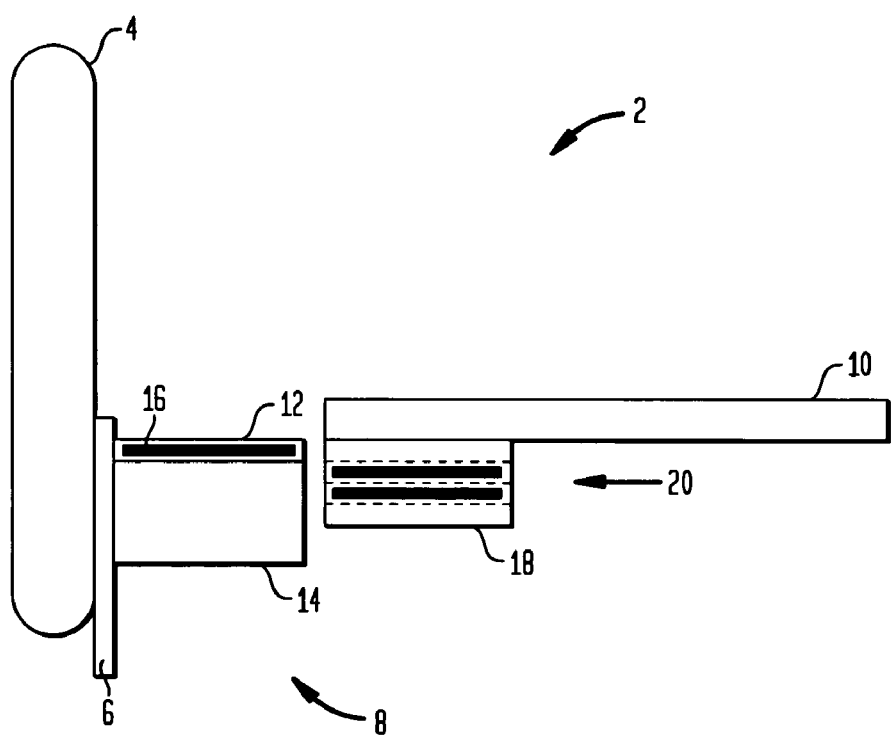
FIG. 1 is a side view of a collimator server system that may be employed in some embodiments of the present invention.

Collimator Storage and Automated Collimator Change:

FIG. 1 depicts a nuclear medical imaging system 2 showing illustrative collimator storage and illustrative automated collimator change components. As shown, an imaging system 2 includes a gantry 4, a rail 6, a detector 8, and a patient handling system 10. In the preferred embodiments, the patient handling system can include a patient support system similar to that described herein below with reference to FIGS. 5-10. In the embodiment shown in FIG. 1, the detector 8 includes a collimator slot 12 and a gamma camera 14. As shown, the collimator slot can be filled with a first collimator 16. Preferably, the gantry 4 is capable of rotating the detector 8 around a center line of the gantry 4, and the rail 6 allows the detector 8 to move toward and away from the center line of gantry 4.

As described in further detail below with reference to FIGS. 5-10, the patient handling system 10 can include an automatic collimator change device or collimator server 18 that is integrated into the patient handling system 10. In various embodiments, the collimator server 18 can have a number of different forms. In some illustrative and non-limiting embodiments, the collimator server includes a number of drawers 20. Each drawer may contain a single collimator, or may be empty.

Figure 2:
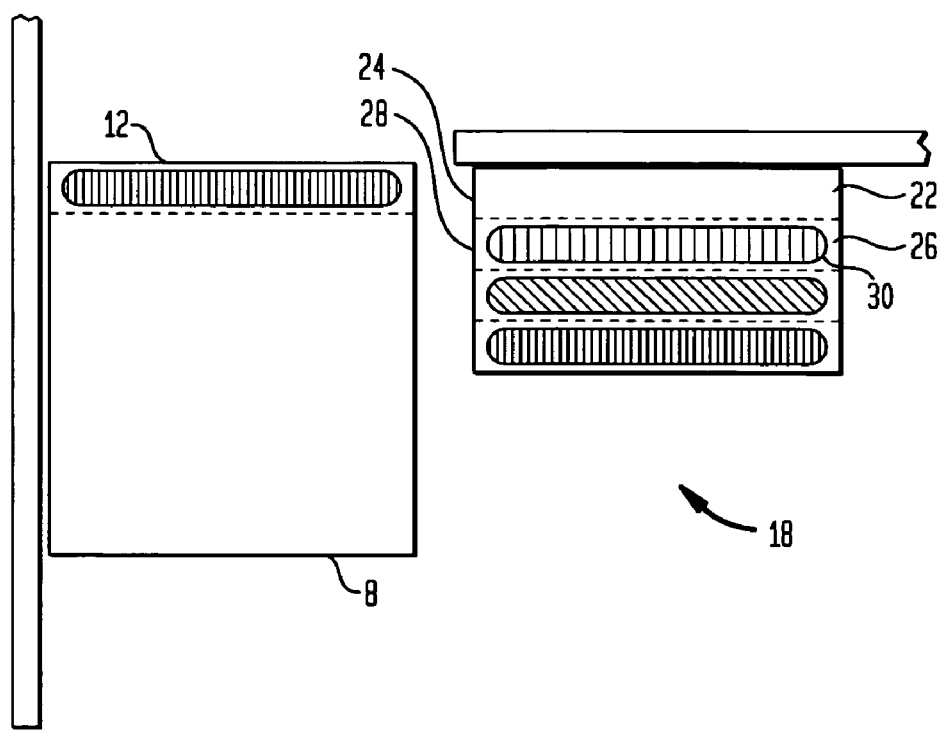
FIG. 2 shows an enlarged side view of a portion of the system shown in FIG. 1.

FIG. 2 shows an enlarged view of the system shown in FIG. 1 depicting further details of the collimator server 18 and the detector 8 according to some illustrative examples. In the illustrated example, a first drawer 22 is shown empty. The first drawer 22 has a front 24. Similarly, the second drawer 26 has a front 28, and it contains a second collimator 30. The first drawer 22 is shown aligned with the collimator slot 12.

Figure 3:
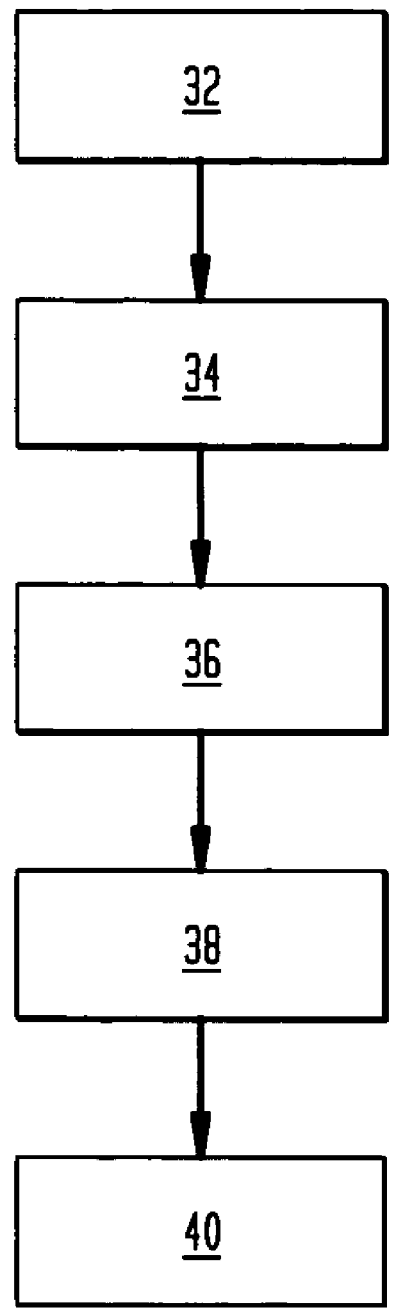
FIG. 3 is a flow chart for an illustrative procedure of removing a collimator using the illustrative embodiment shown in FIG. 1.
Figure 4:
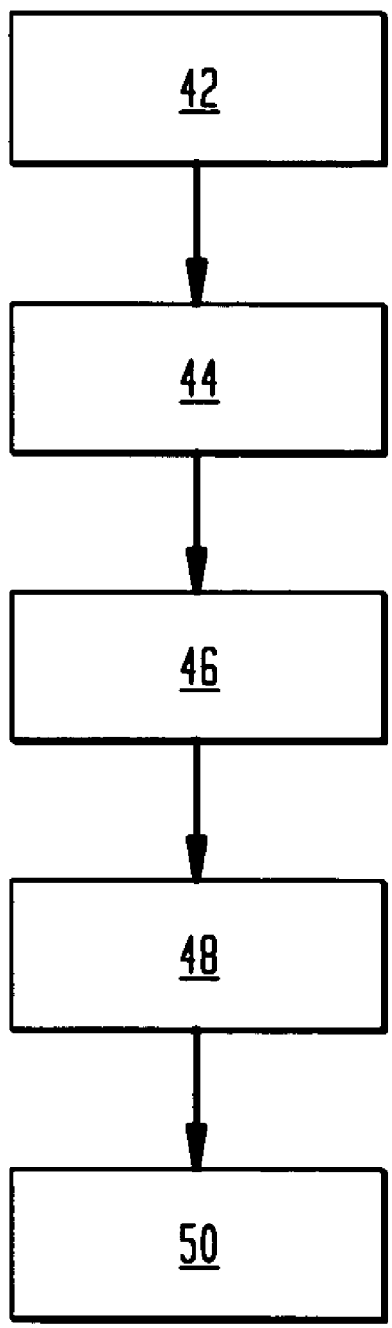
FIG. 4 is a flow chart for an illustrative procedure of mounting a collimator using the illustrative embodiment shown in FIG. 1.

FIG. 3 is a flow chart of some illustrative steps that may be performed to remove a first collimator 16 from collimator slot 12. In step 32, the collimator slot 12 of the detector 8 is aligned with the empty first drawer 22 of collimator server 18. In some examples, this alignment occurs in both rotational (e.g., around the center line of the gantry 4) and translational (e.g., along the rail 6) directions. In step 34, the front 24 of the drawer 22 opens. In step 36, the first collimator 16 is unclamped (e.g., released in any appropriate manner) from the detector 8. In step 38, the first collimator 16 is lifted from collimator slot 12 into drawer 22. In step 40, the front 24 of drawer 22 is closed. Similarly, FIG. 4 is a further flow chart of some illustrative steps that may be performed to mount a second collimator 24 into collimator slot 12. In step 42, the collimator slot 12 is aligned with second drawer 26. In some embodiments, if this is performed directly after step 40, only translation of detector 8 along rail 6 will be necessary. Otherwise, both rotation and translation may be necessary. In step 44, the front 28 of drawer 26 opens. In step 46, the second collimator 30 is lifted from the second drawer 26 onto collimator slot 12. In step 48, the front 28 of second drawer 26 closes. In step 50, the second collimator 30 is clamped (e.g., held in any appropriate manner) into the collimator slot 12.

The above steps can include manual and/or automatic functions. For example, any one or more of these steps could be performed manually, could be triggered manually, and/or could be performed automatically (e.g., at the request of a control system, controller, computer program and/or the like). Thus, any of the procedures can have manual, automatic, or likely both manual and automatic aspects. In preferred embodiments, if a step is performed manually, an additional step by the imaging system's control system is preferably performed to confirm if and/or when that step is performed. For example, if in step 44 the drawer 28 is opened manually, there is preferably a step 49 (not shown) in which the control system of the nuclear medicine imaging system 2 senses that the drawer 28 has been opened. Among other things, this can help to allow automatic functions and/or fail safes to be well coordinated.

In various embodiments, any appropriate mechanical mechanism for moving the collimators (such as, e.g., for the lifting of the first collimator 16 in step 38 or the second collimator 30 in step 46) can be employed. Those in the art would readily appreciate how to employ appropriate mechanisms based on this disclosure. By way of example, mechanisms can include, e.g., hydraulic systems, electromechanical systems and/or the like to carry out the lifting, transferring and/or the like of collimators.

In various embodiments, the foregoing collimator server or automatic collimator change structure could be readily applied in systems with one, two or more detectors. With such a collimator server or automatic collimator change device, a variety of advantages can be achieved, such as, for example: the chance of damaging the collimator or the detector and/or the risk of presenting trouble to the medical technician can be substantially reduced; the time required to mount and/or remove a collimator from a detector can be substantially reduced (e.g., improving patient throughput); the amount of additional floor space needed for mounting and removing collimators can be substantially minimized (e.g., by integrating a collimator server 18 with the patient handling system 10); the mounting or removing of collimators can be performed without moving components by integrating a collimator server 18 into the patient handling system 10, such that the nuclear medicine imaging system can more readily be maintained in standard operating positions.

Preferred Collimator Storage Apparatus Integration with Patient Support:

As described above, both storage and collimator changing have been problematic for most manufacturers, due to the collimator size and weight. Historically, the need to store and change collimators (i.e., because gamma cameras often require multiple sets of collimators specifically designed for a range of energy and resolution) has been difficult and problematic.

In the preferred embodiments, a specialized system and methodology is provided that enables the achievement of an integrated automatic collimator change (IACC) solution without substantial modification, alteration and/or upgrading of a system without such an IACC solution. In this manner, by way of example, customers can gradually enhance existing systems in a methodological and gracefully manner that has limited increases in both cost and/or weight. For example, in some embodiments, an IACC solution can be offered as an upgrade and/or as an option that can be added to a system without the IACC solution, while the cost and weight are substantially applicable to the option itself (i.e., preferably, the system components without the IACC option have little or no extra cost and/or little or no extra weight requirements to accommodate the possible IACC option).

In addition, in preferred embodiments, when an IACC option is provided, the option preferably has minimal or no impact on the operation of the patient support structure (such as, e.g., having minimal or no impact on patient bed deflection).

In addition, in preferred embodiments, in order to easily provide an IACC option, an IACC-less option, and/or an ability to upgrade to an IACC system, a modular and easily configurable structure is provided. For example, in some preferred embodiments a modular and easily configurable support structure is preferably provided. In some preferred examples, the modular and easily configurable support structure includes a collimator support module and a patient bed support module. Preferably, the collimator support module supports a substantial portion of, substantially all, or all of the weight of the IACC collimator storage components. At the same time, the collimator support module preferably cooperates to also support an upper pallet of a patient bed or patient support.

In some preferred embodiments of the invention, the system includes three modular vertical support structures (NB: in this disclosure, the terminology "vertical" is defined, regardless of whether such terminology may have any other common definition(s), to mean generally upright and does not require a specific orientation or require an exact angle or degree of uprightness). Preferably, the modular vertical support structures can be readily configured to include a drive mechanism (such as, e.g., including a drive motor, a screw-shaft drive structure, a pulley drive structure, a timing-belt drive structure and/or the like). Preferably, the modular vertical support structures can also be readily configured to be integrated with (such as, e.g., connected to) a patient support structure.

In some preferred embodiments, the IACC components include a collimator storage unit that is integrated with the patient support (e.g., patient bed) in such a manner as to move together in tandem therewith and/or to move or to be capable of movement independently.

In some preferred embodiments, a basic patient support structure includes one or more lateral frame members that are readily adaptable to reconfigure the system, such as, e.g., by providing telescoping lateral tubular frame members (such as, e.g., hollow tubular frame members, rather than solid frame members). Among other things, the provision of laterally adjustable frame members enables, in some preferred embodiments, the IACC solution to be a configurable option with minimal or no impact on the patient support structure (e.g., with minimal or no change in bed deflection).

Figure 5:
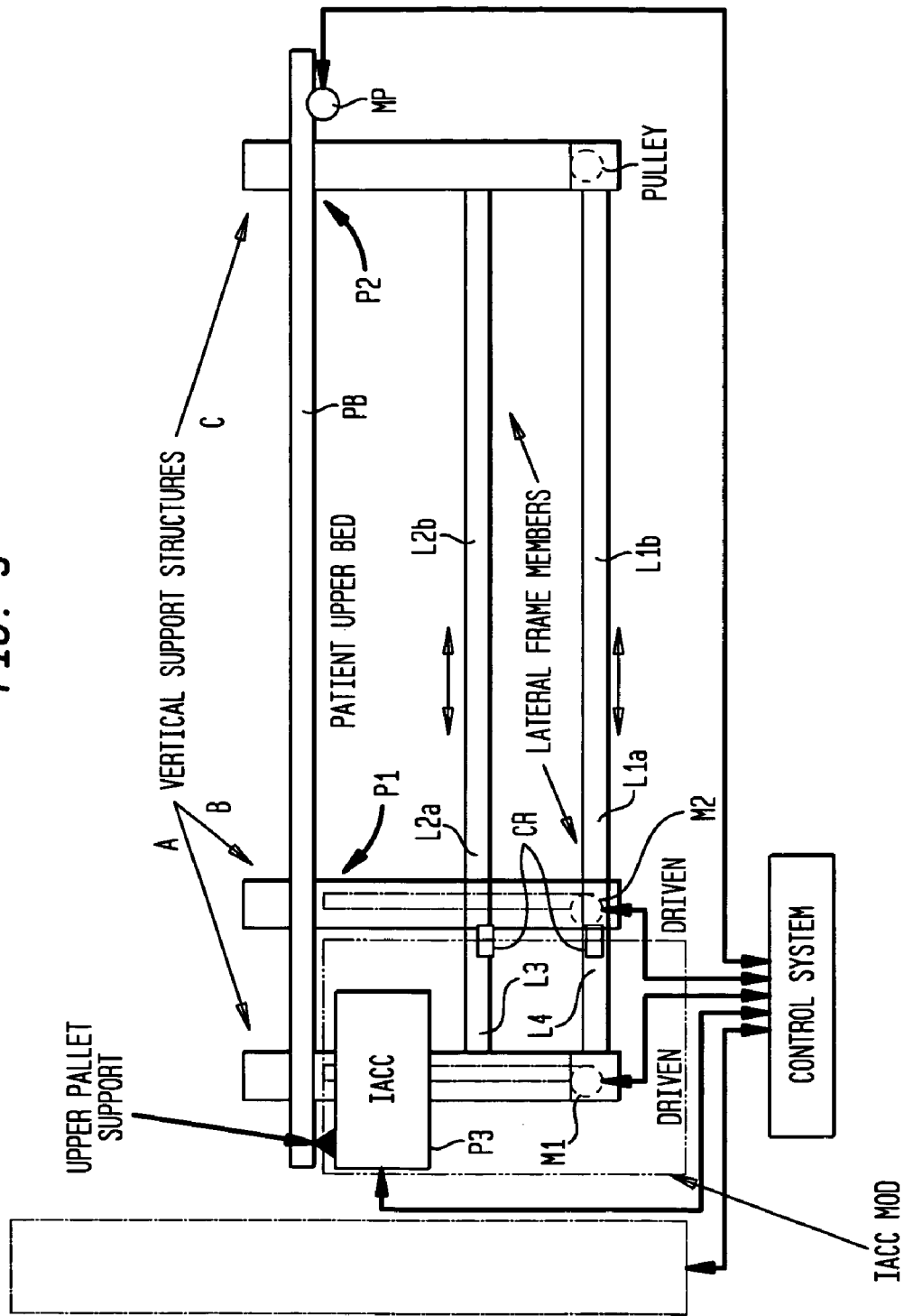
FIG. 5 is a side view showing an embodiment of the present invention including a collimator storage apparatus, collimator server or automatic collimator change apparatus integrated with a patient bed support.

Some illustrative embodiments are shown by way of example in FIGS. 5-10. In this regard, FIG. 5 shows some illustrative embodiments which include three vertical support structures A, B and C. In these illustrative embodiments, the support structures can support a patient bed PB at locations P1 and P2 and the IACC components the location P3. In some of the preferred embodiments, the vertical support structures A, B and C are each configured with either a motor to generate a vertical motion or another mechanism (such as, e.g., a pulley to generate vertical motion from an external drive (such as, e.g. an external belt drive, such as, e.g., a timing belt drive)).

Among other things, the vertical support structures B and C (and the vertical support structure A) can be readily constructed similar to many existing systems, such as, by way of example, similar to the present assignee's (i.e., Siemens Medical Systems, Inc.) existing E.CAM bed supports. In some illustrative embodiments, a first motor M1 and an associated driven structure (such as, e.g., drive shaft(s), drive belt(s), drive screw(s) and/or the like) is used to operate the support structure A for the IACC collimator storage unit (e.g., to raise and/or lower the same), a second motor M2 and an associate driven structure is used to operate the support structure B (i.e., in this example, the support structure B is closer to the gamma camera and gantry than the support structure C) for the patient upper bed PB (e.g., at the left side and/or middle region of the upper bed), and a belt driven pulley or the like is used to operate the support structure C for the patient upper bed PB (e.g., at a right side of the upper bed).

In some embodiments, an IACC collimator storage unit can move a) in tandem with the patient bed during patient imaging (e.g., in a manner that the vertical support structure A can provide support to the patient upper bed PB along with the vertical support structures B and C) or b) independently during collimator change and/or the like (e.g., in a manner that the IACC components may be moved independently of the support structures B and C so as to carry-out or facilitate collimator change and/or the like). In preferred embodiments, when the IACC components are moved tandem, a top of an IACC collimator storage unit supports a gantry-side of the patient bed to, e.g., minimize patient bed deflection, such as shown schematically in FIG. 5. In some embodiments, the IACC support structure can be generally similar to that of the pallet support 200 shown in U.S. Pat. No. 5,619,763, entitled Patient Handling System for Diagnostic Imaging Application, also assigned to Siemens Medical Systems, Inc., the entire disclosure of which is incorporated herein by reference.

In the more preferred embodiments, the vertical support structures B and C are mechanically secured together using lateral frame members. Preferably, the lateral frame members are adjustable lengthwise. In some exemplary embodiments, lateral frame members include inner and outer telescopically received tubular members, which can be readily extended to accommodate a wider distance between the support structures B and C and which can be collapsed to accommodate a narrower distance between the support structures B and C. For example, FIG. 5 shows an illustrative embodiment including two lateral frame members L1 and L2 made up of telescoping pairs of tubular members—i.e., a first pair including members L1a and L1b and a second pair including members L2a and L2b.

As also shown in FIG. 5, in some exemplary embodiments, the vertical support structure A can include lateral frame members L3 and L4 that can be removably coupled to the vertical support structure B using any appropriate attachment mechanisms CR, such as, e.g., connectors, bolts, clamps, rivets, clasps, keyways, locks and/or the like. In yet some other preferred embodiments, the lateral frame members L1 and L2 can be configured to span all of the vertical support members A, B and C. By way of example, in some embodiments, the lateral frame member pairs L2a/L2b and L1a/L1b can extend between the vertical support structures A and C and can be connected to the vertical support structure B in a mid-region of the lateral frame members. By way of example, attachment mechanisms CR could be used, rather than to connect the vertical support member B to the added lateral frame member segments L3 and L4, to connect the vertical support member B along the length of the lateral frame members which span between the support structure A to the support structure C.

Accordingly, in the preferred embodiments, the lateral frame members can be extended and/or retracted in such a manner as to modify a center-to-center distance between the vertical support structures B and C, such as to accommodate the inclusion (i.e., by a narrower separation as shown, e.g., in FIG. 5) or the exclusion (i.e., by a wider separation as shown, e.g., in FIG. 6) of the IACC module shown in FIG. 5 (i.e., to accommodate an IACC option).

In this manner, in the preferred embodiments a system is provided that creates a modular integrated automatic collimator change option or a modular collimator server option. In this regard, FIG. 5 depicts illustrative IACC module components within the double-dashed line box labeled at IACC MOD. With the structure of the preferred embodiments, the system can readily accommodate alterations to include and/or to remove the IACC option using a reusable modular vertical support structure that advantageously a) distributes the weight of the IACC collimator server or storage components and b) distributes the weight of the patient bed in such a manner that maximum loads can be substantially reduced. By way of example, in some embodiments, the maximum loads that may be imparted on each individual support structure A, B and C in some embodiments can be maintained below about 1000 pounds, and, more preferably, below about 800 pounds, and, in some embodiments, only up to about 600 pounds. In addition, preferred embodiments also use the IACC vertical support structure (either via an IACC storage unit or collimator server itself and/or via a support arm or the like mounted therewith on the vertical support structure A) to support a left side of the patient bed or the like (i.e., which can help to, e.g., minimize bed deflection).

Figure 6:
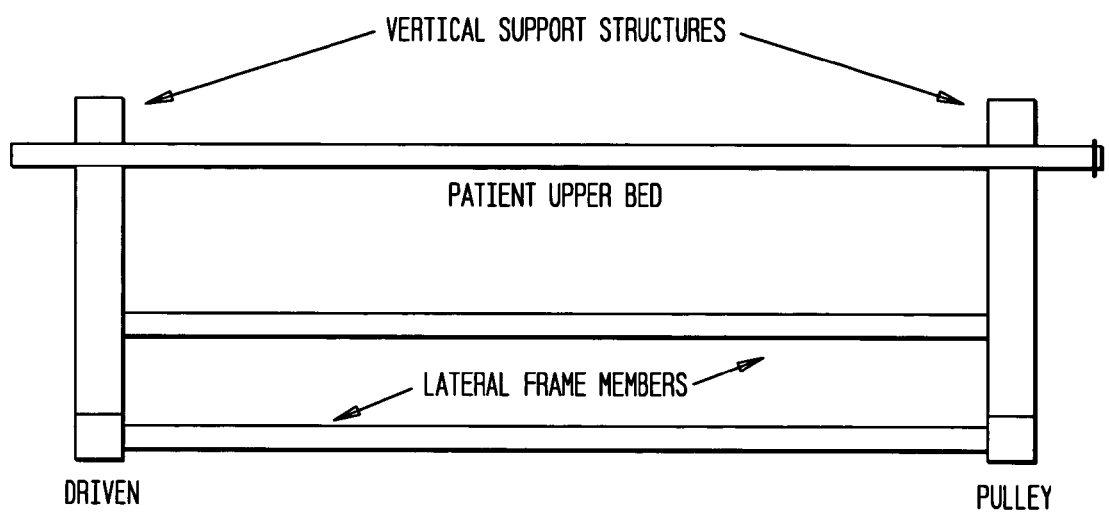
FIG. 6 is a side view showing an embodiment of the present invention including a patient bed support configured without an integrated collimator storage apparatus, collimator server or automatic collimator change option.

In this manner, the weight of the overall assemblies shown in FIG. 5 (i.e., including the IACC module) and/or shown in FIG. 6 (i.e., not including the IACC module) can be substantially minimized due to, e.g., a corresponding reduction in the amount of force imparted on the structural members. In addition, the embodiments shown in FIGS. 5 and 6 should also provide a less costly alternatives in which the subassemblies can be readily manufactured using, for example, lighter weight materials, such as, e.g., sheet metal (such as, e.g., roll-formed and/or otherwise formed sheet materials) and/or tubular metal components (e.g., tubular steel components), as compared to costly heavy duty machined details that may otherwise be required in other systems or applications.

In the preferred embodiments, the drive mechanisms providing vertical lift to the patient support or bed and/or to the IACC collimator server or storage unit preferably include screw shafts that are driven directly or indirectly (such as, e.g., via pulleys) from the output of a motor (such as, e.g., an electronic motor, a stepper motor and/or the like). However, a variety of other lift mechanisms could be employed in less preferred embodiments, such as, e.g., hydraulic cylinders, mechanical linkages and/or the like. However, it should be appreciated that various other drive mechanisms may have significant disadvantages. By way of example, while a patient support structure (e.g. patient bed) could potentially be raised and/or lowered using an expandable scissor-type linkage or mechanism, such mechanisms can experience a very high level of stress, such as, e.g., approximately 6 to 8 times the level of stress (which can be, e.g., as much as about 8000 pounds in some examples), which, thus, would require large, heavy duty machined steel and/or the like structural components.

The preferred embodiments described herein can provide one or more, preferably all, of the following advantages: a reduction in assembly standard costs; a reduction in assembly weight; a reduction in patient support (e.g., patient bed) deflection; and/or the like advantages. Moreover, the preferred embodiments also enable, one or more, preferably all of the following other advantages: the achievement of a scalable, modular solution that allows the cost (e.g., control and weight) to be distributed within respective sub-assemblies; the reduction of bed deflection to that of systems in which the bed does not support the collimators (such as, e.g., similar to that the present assignee's E.CAM devices); and/or the reduction in the overall assembly weight, such as, e.g., by using basic sheet metal and/or tubular constructions.

Figure 7:
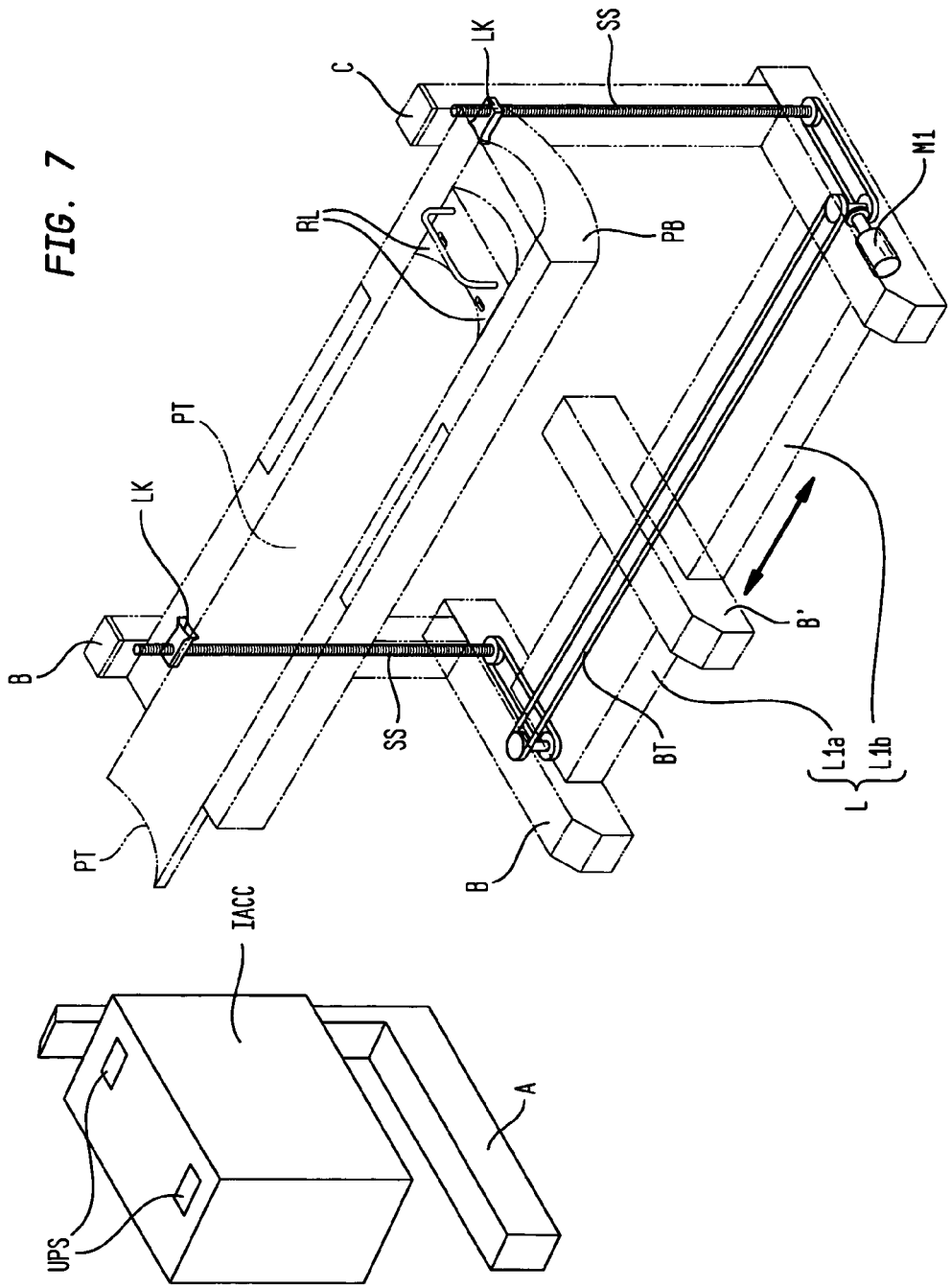
FIG. 7 is a perspective view showing illustrative patient support components according to some preferred embodiments of the invention.

Illustrative Patient Support Components:

FIG. 7 shows an illustrative system that can be employed in some illustrative embodiments. The device shown in FIG. 7 is generally similar to that shown in FIGS. 5-6. In the embodiment shown in FIG. 7, the vertical support structures A, B, C provide a substantially cantilevered support of the patient bed PB and the IACC collimator server or storage unit as shown. In this regard, the patient bed is supported for generally vertically reciprocated motion up-and-down via the rotated vertical screw shafts SS via the support linkages LK which threadingly engage the screw shafts SS in a manner to move up-and-down along with rotation of the screw shafts SS. Although not shown in FIG. 7, the vertical support structure A preferably includes a similar, but independent, motor, drive belts and screw shaft components. As shown, the screw shafts SS are preferably connected together by a belts BT (such as, e.g., timing belts) and are preferably driven synchronously by means of the drive motor M1. Although the drive motor is shown in FIG. 7 as being located proximate the vertical support structure C in this illustrative embodiment, it is contemplated that the location of the motor can be varied based on circumstances. As a result, the rotation of the drive motor M1 raises or lowers the upper patient bed PB by rotating the screw shafts SS. In this embodiment; the direction of the rotation of the drive motor M1, thus, determines whether the upper patient bed is raised or lowered.

In the embodiment shown in FIG. 7, the patient bed PB includes a curved patient pallet PT that is supported by, and rolls upon, rollers RL (while two rollers are shown, a plurality of additional rollers are preferably included beneath the pallet upon the patient bed PB). The patient pallet PT receive a patient thereon in a reclined orientation. The patient pallet PT is moveable lengthwise back and forth with respect to the patient bed, which movement may be imparted, e.g., via a drive motor (not shown) and/or manually via a handle. As shown in FIG. 7, the IACC collimator server or storage unit preferably includes at least one upper pallet support UPS that may provide support under the patient bed PB. In this manner, the IACC collimator server or storage unit is preferably completely or substantially completely received under the patient bed PB. In some embodiments, the IACC collimator server or storage unit may extend outward some extent or may be situated laterally to the side of the patient bed. In the latter instances, the UPS is preferably adapted to still provide support for the patient bed and may also include at least one roller for receiving the pallet PT.

As shown in FIG. 5, the drive motors M1, M2, and MP (i.e., motor MP is provided for moving the pallet) are preferably connected to, and controlled by, a common control system. The controller system may include one or more computer, controller, processor and/or the like, and may include an appropriate human interface, such as, e.g., a control panel, a hand-held control or the like. As also shown in FIG. 5, the control system may also be used to control other operations of the IACC system, the gantry and/or the like.

Among other things, the control system may be used to provide appropriate synchronization between the motors M1 and M2 in embodiments employing an IACC module. In addition, the control system may be used to provide asynchronous and/or independent operation of the motors M1 and M2, such as, e.g., during collimator changing operations. Various embodiments may employ a variety of different means for coordinating the movement of the motors M1 and M2. For example, in some embodiments, the vertical support structures support positions can be matched (i.e., coordinated for a desired relative movement) and/or compensated for (e.g., adjusted based on relative movement), such as, e.g., based on integral and/or differential position non-linearity, by means of, for example, a) a lookup table, b) linear encoders (determining, e.g., support linkage LK positions or the like), c) rotary encoders (determining, e.g., rotational positions of acme screw shafts, pulleys, drive shafts of motors or the like), d) pressure and/or strain gauges (determining, e.g., whether an uneven load is applied to one or more of the vertical support structures), e) position detectors (such as, e.g., photodetectors or the like for detecting patient support position or the like) and/or d) any other means that can be employed for automatic control based on support structure component position.

Figure 8A:
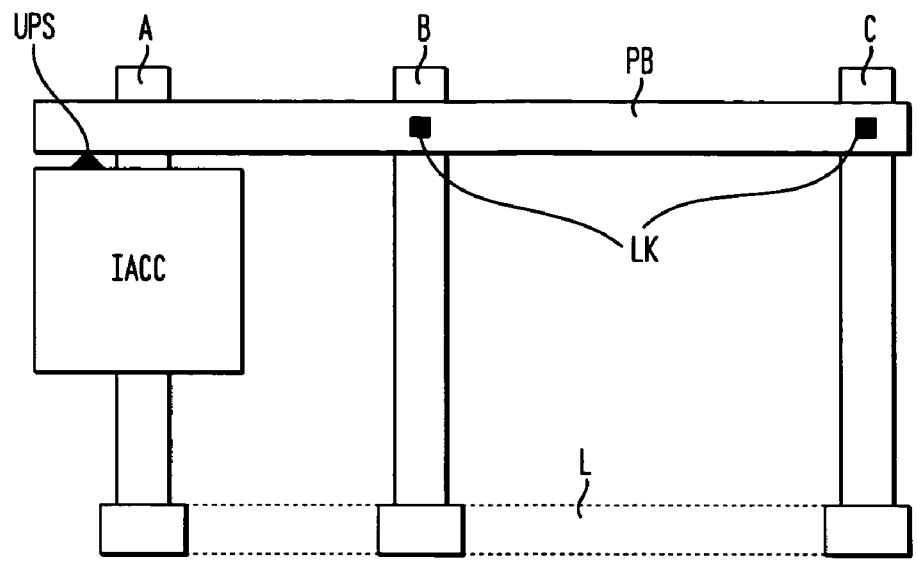
FIGS. 8(A)-(B) and 9(A)-9(B) demonstrate illustrative synchronous and asynchronous or independent control that can be employed in some illustrative embodiments.
Figure 8B:
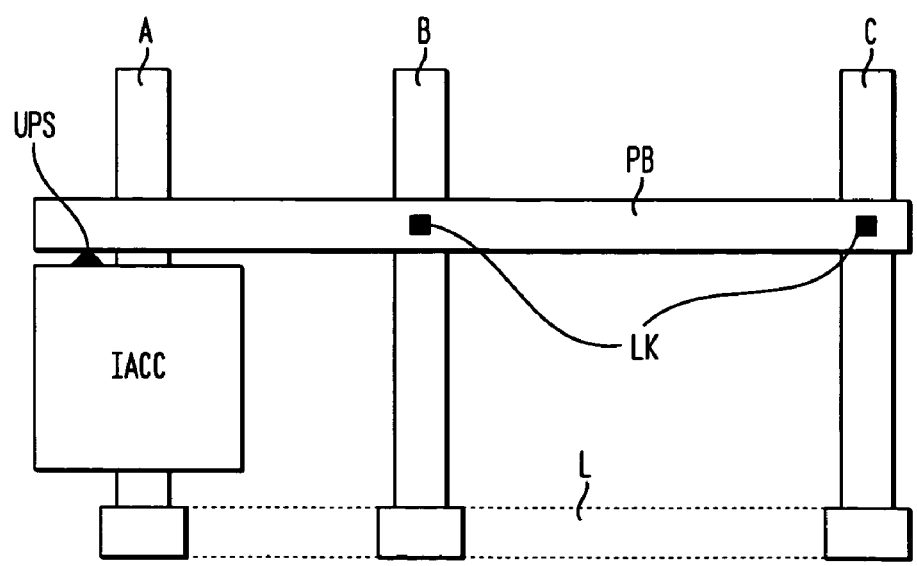
Figure 9A:
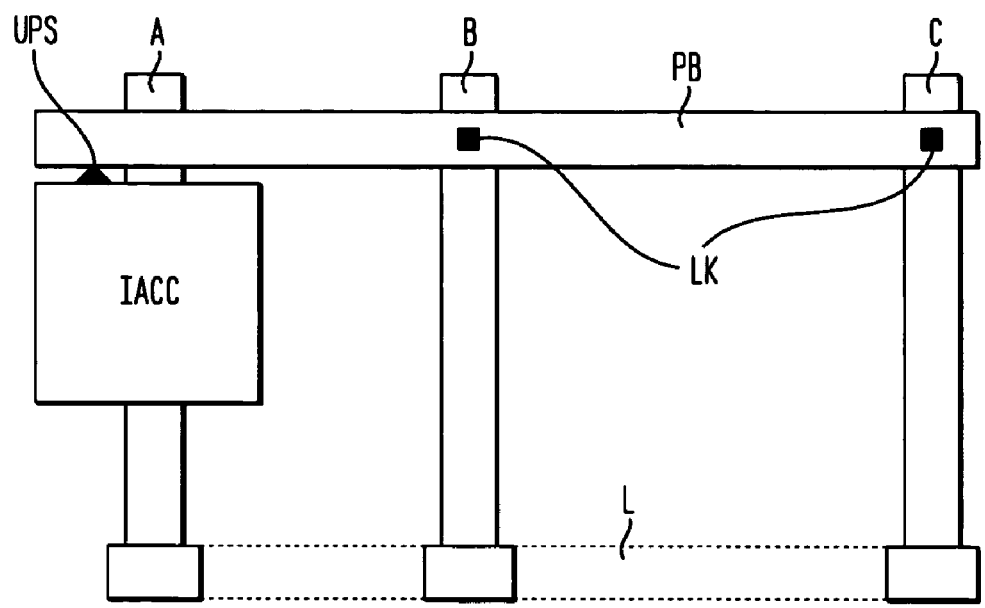
Figure 9B:
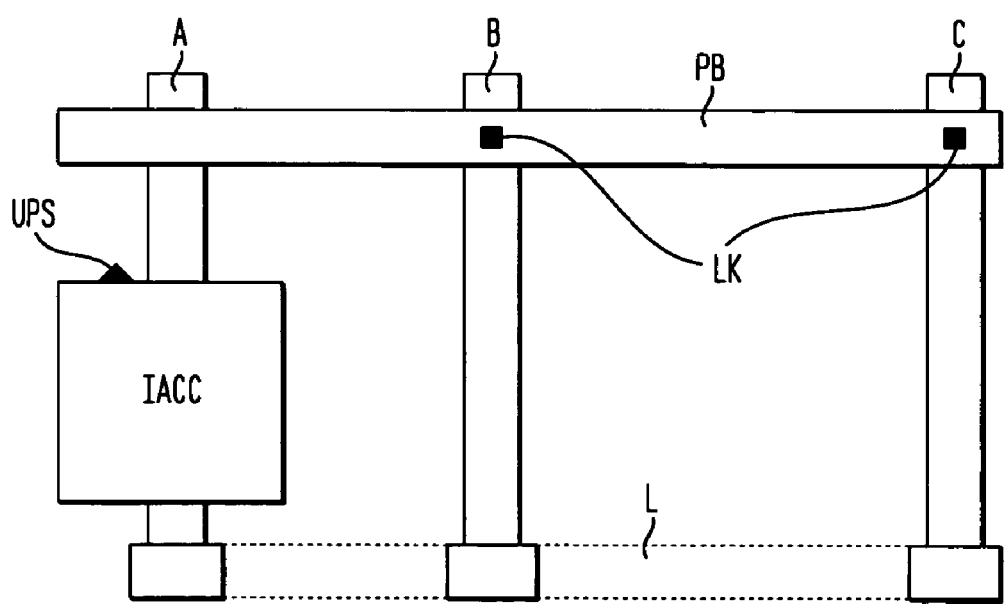

For reference, FIGS. 8(A)-(B) and 9(A)-9(B) demonstrate illustrative synchronous and asynchronous or independent control that can be employed in some illustrative embodiments. In this regard, FIGS. 8(A)-8(B) demonstrate embodiments in which the IACC collimator server or storage unit and the patient support or patient bed PB are moved synchronously. For example, FIG. 8(A) shows the IACC collimator server or storage unit at a like relative position with respect to the bottom of the patient support or bed PB to the relative position shown in FIG. 8(B). In some illustrative embodiments, the vertical support structure A is not connected to the patient support or bed via a support linkage LK in a like manner to the vertical support structures B and C, but rather the top of the IACC collimator server or storage unit includes an upper pallet support UPS that can move to a supporting position as shown. When the UPS is moved in tandem with the patient support or bed PB, the UPS can help to support the same. However, in some embodiments, the UPS is preferably not fixedly attached to the patient support or bed PB (or is readily released from attachment) to enable the IACC collimator server or storage unit to also be moved independently with respect to the patient support or bed PB. In this regard, FIG. 9(A) illustrates a positional arrangement like FIG. 8(A), but in movement to the positional arrangement shown in FIG. 8(B), the IACC collimator server or storage unit is moved independently from the patient support to a separated position. For example, this independent movement may be helpful, in some embodiments, to facilitate operation of the IACC collimator server or storage unit to change collimators and/or for other purposes.

Figure 10:
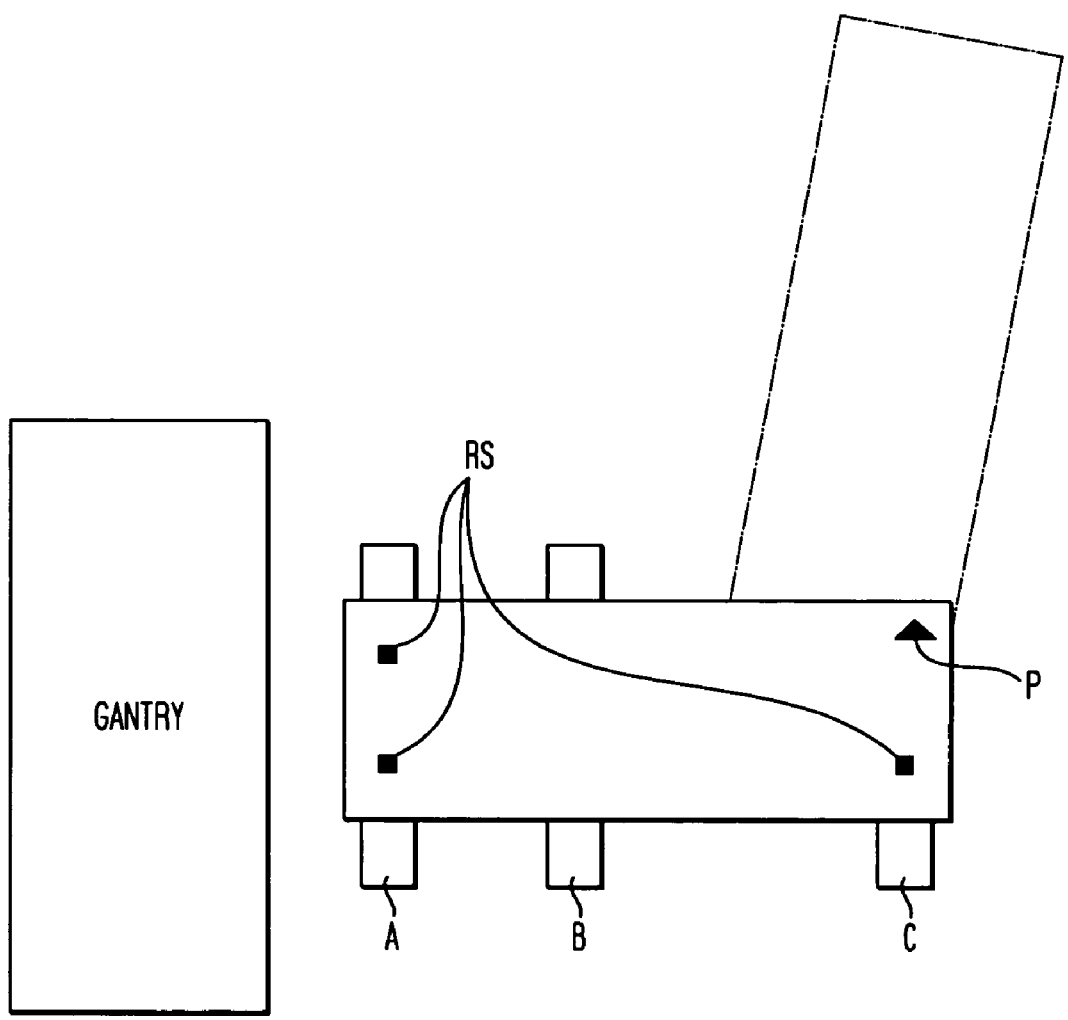
FIG. 10 is a top view of an illustrative patient support system having an integrated automatic collimator change system and patient bed that can be rolled aside under certain circumstances.

In some embodiments, the integrated automatic collimator change option and patient support components can be fixedly attached to a floor proximate a gantry and/or can include rollers or the like to enable the system to be rolled away as needed. For example, FIG. 10 depicts a top view of an illustrative embodiment in which the combined integrated automatic collimator change option components (e.g., the collimator server or storage unit) and the patient support structure can be readily rolled out of the way as needed. In this regard, for example, the base of the patient support system can include rollers RS to facilitate rolling as shown. In some embodiments, one corner of the base can be pivotally, but fixedly anchored to the floor at location P in a manner to enable pivoting of the patient support system from the normal use position proximate the gantry as shown in solid lines in FIG. 10 to an out-of-the-way position shown in dashed lines in FIG. 10. Among other things, this embodiment can facilitate placement of a patient proximate the gantry on a separate patient support or the like, such as, e.g., on a separately wheeled in hospital bed or the like.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (for example, various aspects in different embodiments can be combined together when appropriate in various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. A modular patient support system for a nuclear medical imaging system, comprising:
    a patient support;
    a plurality of support structures for supporting the weight of said patient support; wherein
    at least one of said support structures is modularly removable from and connectable to said modular patient support system to accommodate an imaging option change of the nuclear medical imaging system, wherein said option change is the addition or removal of a collimator server.

2. The modular patient support system of claim 1, wherein said support structures include vertical drives.

3. An assembly of modular components for nuclear imaging applications, comprising:
    a patient support;

at least two vertical motion support structures solely supporting the weight of said patient support in a first use condition of a nuclear medical imaging system; and at least one modular vertical support structure removably connectable to support the weight of said patient support along with said at least two vertical motion support structures in a second use condition of a nuclear medical imaging system.

4. The assembly of modular components for nuclear imaging applications of claim 3, wherein said first use condition is a condition without an automated collimator changer and said second use condition is a condition with an automated collimator changer.

5. The assembly of modular components for nuclear imaging applications of claim 3, wherein said at least one modular vertical support structure includes a drive motor.

6. The assembly of modular components for nuclear imaging applications of claim 5, wherein said at least one modular vertical support structure includes a pulley driven by said drive motor.

7. The assembly of modular components for nuclear imaging applications of claim 3, wherein said at least two vertical motion support structures include a plurality of vertical support structures that are connected together via at least one lateral frame member that adjusts in length to accommodate different vertical support structure use positions.

8. The assembly of modular components for nuclear imaging applications of claim 7, wherein each said at least one lateral frame member telescopes to adjust in length.

9. A patient support system for a nuclear medical imaging system, comprising:
a patient support;
an integrated collimator changer storage unit located under said patient support and supported substantially by a first vertical motion support structure; and
at least one other vertical motion support structure supporting an end of said patient support distal from the first vertical motion support structure.

10. The patient support system for a nuclear medical imaging system of claim 9, wherein said integrated automated collimator changer storage unit includes a support for said patient support.

11. The patient support system for a nuclear imaging system of claim 9, wherein said at least one other vertical motion support structure includes two vertical motion support structures, one driven via a first motor and one driven via a pulley, and wherein said first vertical motion support structure is driven via a second motor.

12. A method of modifying a patient support system without an integrated collimator server to create a patient support system with an integrated collimator server, comprising:
a) providing a patient support for an imaging system and at least one vertical motion support structure supporting said patient support in a first use condition without an integrated collimator server;
b) modifying said patient support system to include an integrated collimator server underneath said patient support by adding at least one additional vertical motion support structure underneath said patient support that supports a substantial portion of the weight of a collimator server located underneath said patient support and that helps support a portion of the patient support proximate a gantry.

13. The method of claim 12, wherein said step of modifying includes upgrading an existing patient support system after purchase and receipt by a consumer.

14. The method of claim 12, wherein said step of modifying includes adapting a patient support system before purchase by a consumer.

15. The method of claim 12, wherein said step of modifying further includes laterally moving said at least one vertical motion support structure supporting said patient support from a first position corresponding to said first use condition without an integrated collimator server to a second position corresponding to a second use condition with an integrated collimator server.

16. The method of claim 12, wherein said at least one vertical motion support structure supporting said patient support includes plural vertical motion support structures, including a first driven via a motor and a second driven via a pulley.

17. The method of claim 12, wherein said patient support is a patient bed and wherein said integrated collimator server includes an upper pallet support for supporting a gantry side of said bed during imaging.

18. A method of integrating an automated collimator change storage device with a patient support system, comprising:
a) providing a patient support;
b) providing a plurality of vertical support structures underneath said patient support with:
i) a first of said plurality of vertical support structures supporting a substantial portion of the weight of an automated collimator change storage device underneath said patient support at a location proximate to a gantry of a nuclear medical imaging system; and
ii) a second of said plurality of vertical support structures supporting at least a portion of said patient support at a location distal from a gantry of a nuclear medical imaging system.

19. The method of claim 18, wherein said first and second of said plurality of vertical support structures include separate drives.

20. The method of claim 19, wherein said separate drives include separate drive motors that rotate respective vertical screw shafts.

21. The method of claim 20, further including a control system configured to operate said drive motors in tandem.

22. The method of claim 20, further including a control system configured to operate said drive motors in tandem and independently, such that said automated collimator change storage device moves either in tandem with or independently from said patient support.

23. The method of claim 20, further including a control system configured to move support members of said vertical support structures such that positions of said support members can be coordinated using at least one of a) a lookup table, b) an encoder, c) a pressure or strain gauge and d) a position detector.

24. A nuclear medicine imaging system, comprising:
a gantry;
a detector attached to said gantry, having a gamma camera and at least one collimator location;
a patient handling system having a patient support;
a collimator server integrated into the patient handling system and storing a number of collimators beneath said patient support, said collimator server including an independent support that supports substantially all of the weight of said collimator server;
said collimator server being adapted to enable
i) loading of collimators into the collimator location,
ii) removing collimators from the collimator location, and
iii) storing collimators beneath said patient support.

25. The nuclear medicine imaging system of claim 24, wherein the collimator server further includes means for supporting said patient support at a position proximate to said gantry.

26. The nuclear medicine imaging system of claim 24, wherein said independent support includes a vertical support structure having an independent vertical drive mechanism from a vertical drive mechanism of a vertical support structure that supports said patient support at a position distal from said gantry.

27. The nuclear medicine imaging system of claim 24, wherein said independent support for the collimator server supports a substantial portion of the weight of all collimators stored thereon as well as a portion of the patient support so as to limit deflection of the patient support.

28. A patient support system for a nuclear medical imaging system, comprising:
  a patient support;
  a collimator storage unit located under said patient support;
  a first support means for supporting substantially all of the weight of said collimator storage unit; and
  a second support means for supporting said patient support at least at a position distal from a gantry of the nuclear medical imaging system.

29. The patient support system according to claim 28, wherein said first support means includes means for supporting said patient support at a position proximate a gantry of the nuclear medical imaging system.

30. The patient support structure according to claim 28, wherein said second support means includes two vertical support structures.

31. The patient support structure according to claim 30, further including at least one laterally extendable frame member mounted between said two vertical support structures.

* * * * *